US010918911B2

(12) United States Patent
Martin (10) Patent No.: US 10,918,911 B2
(45) Date of Patent: *Feb. 16, 2021

(54) SYSTEM AND METHOD FOR PROVIDING A COACH WITH LIVE TRAINING DATA OF AN ATHLETE AS THE ATHLETE IS PERFORMING A CYCLING WORKOUT

(71) Applicant: FINISH TIME HOLDINGS, LLC, Plano, TX (US)

(72) Inventor: Todd Martin, Lexington, OH (US)

(73) Assignee: FINISH TIME HOLDINGS, LLC, Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/023,913

(22) Filed: Sep. 17, 2020

(65) Prior Publication Data

US 2021/0001179 A1 Jan. 7, 2021

Related U.S. Application Data (63) Continuation of application No. 16/844,692, filed on Apr. 9, 2020, now Pat. No. 10,792,537, which is a continuation of application No. 16/443,741, filed on Jun. 17, 2019, now Pat. No. 10,799,763, which is a continuation of application No. 15/870,858, filed on
(Continued)

(51) Int. Cl.
| | |
|---|---|
| A63B 24/00 | (2006.01) |
| A63B 71/06 | (2006.01) |
| G16H 20/30 | (2018.01) |
| G06Q 10/06 | (2012.01) |
| H04M 1/725 | (2021.01) |

(52) U.S. Cl.
CPC ...... *A63B 24/0075* (2013.01); *A63B 24/0062* (2013.01); *A63B 71/0616* (2013.01); *G06Q 10/06* (2013.01); *G16H 20/30* (2018.01); *H04M 1/72522* (2013.01)

(58) Field of Classification Search
None
See application file for complete search history.

(56) References Cited

U.S. PATENT DOCUMENTS

| | | |
|---|---|---|
| 2,146,304 A | 2/1939 | Lee |
| 4,612,623 A | 9/1986 | Bazarik |

(Continued)

FOREIGN PATENT DOCUMENTS

| | | |
|---|---|---|
| JP | 5653038 B2 | 1/2005 |
| WO | WO 2008/030484 | 3/2008 |

OTHER PUBLICATIONS

Earthday 5K Run [online]; Retrieved from the Internet: <URL: http://web.archive.org/web/20100616133511/http://www.compuscore.com/cs2010/april/earthday.htm> [retrieved Apr. 30, 2013]; Jun. 16, 2010.

(Continued)

*Primary Examiner* — Ronald Laneau
(74) *Attorney, Agent, or Firm* — Jason H. Vick; Sheridan Ross, PC (57) ABSTRACT

An athlete tracking system and method for tracking an athlete during training sessions. The system includes a mobile tracking device wearable around a portion of the athlete's head, and a training log server for maintaining an athlete profile that includes a training record updatable by the athlete and a training plan supplied by a coach.

20 Claims, 5 Drawing Sheets

Related U.S. Application Data

Jan. 13, 2018, now Pat. No. 10,322,314, which is a continuation of application No. 15/162,613, filed on May 23, 2016, now Pat. No. 9,889,340, which is a continuation of application No. 14/054,879, filed on Oct. 16, 2013, now Pat. No. 9,345,948.

(60) Provisional application No. 61/715,847, filed on Oct. 19, 2012.

(56) References Cited

U.S. PATENT DOCUMENTS

| | | | |
|---|---|---|---|
| 4,831,242 A | 5/1989 | Englehardt et al. | |
| 6,002,982 A | 12/1999 | Fry | |
| 6,013,007 A | 1/2000 | Root et al. | |
| 6,059,692 A | 5/2000 | Hickman | |
| 6,442,505 B1 | 8/2002 | Lee | |
| 6,463,385 B1 | 10/2002 | Fry | |
| 6,608,563 B2 | 8/2003 | Weston et al. | |
| 6,837,827 B1 | 1/2005 | Lee et al. | |
| 6,985,875 B1 | 1/2006 | Wolf | |
| 7,047,214 B2 | 5/2006 | Wolf | |
| 7,092,846 B2 | 8/2006 | Vock et al. | |
| 7,158,689 B2 | 1/2007 | Valleriano et al. | |
| 7,254,516 B2 | 8/2007 | Case, Jr. et al. | |
| 7,395,167 B2 | 7/2008 | Frolik | |
| 7,534,206 B1 | 5/2009 | Lovitt et al. | |
| 7,800,646 B2 | 9/2010 | Martin | |
| 7,876,352 B2 | 1/2011 | Martin | |
| 7,934,983 B1 | 5/2011 | Eisner | |
| 7,988,599 B2 | 8/2011 | Ainsworth et al. | |
| 8,065,342 B1 | 11/2011 | Borg et al. | |
| 8,432,270 B2 | 4/2013 | Lee et al. | |
| 8,649,890 B2 | 2/2014 | Martin | |
| 8,719,202 B1 | 5/2014 | Maeng | |
| 8,784,115 B1 | 7/2014 | Chuang | |
| 8,968,156 B2 | 3/2015 | Ellis et al. | |
| 8,988,240 B2 | 3/2015 | Burton et al. | |
| 9,079,059 B2 | 7/2015 | Cardoso, Jr. et al. | |
| 9,087,454 B2 | 7/2015 | Crivello et al. | |
| 9,141,087 B2 | 9/2015 | Brown et al. | |
| 9,144,165 B2 | 9/2015 | Yu et al. | |
| 9,317,660 B2 | 4/2016 | Burich et al. | |
| 9,345,948 B2 | 5/2016 | Martin | |
| 9,392,941 B2 * | 7/2016 | Powch | G09B 5/02 |
| 9,889,340 B2 | 2/2018 | Martin | |
| 10,124,234 B2 | 11/2018 | Martin | |
| 10,322,314 B2 | 6/2019 | Martin | |
| 10,643,483 B2 * | 5/2020 | Rauhala | G06Q 10/0639 |
| 10,792,537 B2 | 10/2020 | Martin | |
| 2002/0193923 A1 | 12/2002 | Toyama et al. | |
| 2003/0109972 A1 | 6/2003 | Tak | |
| 2004/0117072 A1 | 6/2004 | Takeda | |
| 2004/0201738 A1 | 10/2004 | Moores, Jr. et al. | |
| 2005/0195094 A1 | 9/2005 | White | |
| 2006/0064731 A1 | 3/2006 | Kahle et al. | |
| 2006/0125930 A1 | 6/2006 | Mindrum et al. | |
| 2006/0136173 A1 | 6/2006 | Case, Jr. et al. | |
| 2006/0235765 A1 | 10/2006 | David | |
| 2006/0287930 A1 | 12/2006 | Wolf et al. | |
| 2007/0118239 A1 | 5/2007 | Zimmermann et al. | |
| 2007/0158949 A1 | 7/2007 | Le Gars et al. | |
| 2007/0208544 A1 | 9/2007 | Kulach et al. | |
| 2007/0219059 A1 | 9/2007 | Schwartz et al. | |
| 2007/0288157 A1 | 12/2007 | Peterman | |
| 2008/0052349 A1 | 2/2008 | Lin | |
| 2008/0109158 A1 | 5/2008 | Huhtala et al. | |
| 2008/0252297 A1 | 10/2008 | Miglioranza | |
| 2008/0300914 A1 | 12/2008 | Karkanias et al. | |
| 2009/0011907 A1 | 1/2009 | Radow et al. | |
| 2009/0141138 A1 | 6/2009 | DeAngelis | |
| 2009/0192391 A1 | 7/2009 | Lovitt et al. | |
| 2009/0231147 A1 | 9/2009 | Peck et al. | |
| 2009/0233771 A1 | 9/2009 | Quatrochi et al. | |
| 2009/0278707 A1 | 11/2009 | Biggins et al. | |
| 2010/0004097 A1 | 1/2010 | D'Eredita | |
| 2010/0036736 A1 | 2/2010 | McGee et al. | |
| 2010/0062818 A1 | 3/2010 | Haughay, Jr. et al. | |
| 2010/0088023 A1 | 4/2010 | Werner | |
| 2010/0149305 A1 | 6/2010 | Catchpole et al. | |
| 2010/0151996 A1 | 6/2010 | Alten et al. | |
| 2010/0184564 A1 | 7/2010 | Molyneux et al. | |
| 2010/0191827 A1 | 7/2010 | Martin | |
| 2010/0210421 A1 | 8/2010 | Case, Jr. et al. | |
| 2010/0210975 A1 | 8/2010 | Anthony, III et al. | |
| 2011/0003664 A1 | 1/2011 | Richard | |
| 2011/0090092 A1 | 4/2011 | Birrell et al. | |
| 2011/0098928 A1 | 4/2011 | Hoffman et al. | |
| 2011/0133918 A1 | 6/2011 | Lee et al. | |
| 2011/0152695 A1 | 6/2011 | Granqvist et al. | |
| 2011/0250937 A1 | 10/2011 | Hubbard et al. | |
| 2011/0310389 A1 | 12/2011 | Clark et al. | |
| 2012/0139731 A1 | 6/2012 | Razoumov et al. | |
| 2012/0166044 A1 | 6/2012 | Battlogg et al. | |
| 2012/0253485 A1 | 10/2012 | Weast et al. | |
| 2012/0290109 A1 | 11/2012 | Engelberg et al. | |
| 2013/0053218 A1 | 2/2013 | Barker | |
| 2013/0066449 A1 * | 3/2013 | Verstegen | G16H 20/30 700/91 |
| 2013/0138734 A1 | 5/2013 | Crivello et al. | |
| 2013/0218832 A1 | 8/2013 | Young et al. | |
| 2013/0249708 A1 | 9/2013 | Moll-Carrillo et al. | |
| 2014/0156041 A1 | 6/2014 | Martin | |
| 2014/0266160 A1 | 9/2014 | Coza | |
| 2015/0061891 A1 | 3/2015 | Oleson et al. | |
| 2015/0178325 A1 | 6/2015 | Winchester et al. | |
| 2016/0358504 A1 | 12/2016 | Powch et al. | |
| 2017/0007882 A1 | 1/2017 | Werner | |
| 2019/0299060 A1 | 10/2019 | Martin | |

OTHER PUBLICATIONS

Franz, Kelsch "Training Log Online Options" http://www.blog.ultracycle.net/2010/05/training-log-online; [retrieved Dec. 2014]; May 12, 2010.

Nashbar, NB-WC Wireless Computer Owner's Manual; accessed at http://www.nashbar.com/images/nashbar/web/PDFs/NB-WC%20Wireless%20Computer.pdf; (retrieved Dec. 2014); Sep. 2014.

Polar, Polar CS5500 User Manual; http://www.polar.com/e_manuals/CS500/Polar_CS500_user_manual_English/manual.pdf; Jan. 2011.

U.S. Appl. No. 61/705,232, filed Sep. 25, 2012.

STRAVA.com "GPS Bike Routes and Cycling Training Log" http://www.strava.com, archived Jan.-Apr. 2010 (retrieved Dec. 2014).

USA Triathlon—FAQ [online], Retrieved from the Internet: <URL: http://web.archive.org/web/20090511172916/http://triathlon.teamusa.org/content/index/666> [retrieved Jun. 18, 2013]; May 11, 2009.

Examination Report for New Zealand Application No. 600383, dated May 8, 2013.

Examination Report for New Zealand Application No. 600383, dated Jul. 1, 2013.

Examination Report for New Zealand Application No. 612035, dated Jun. 23, 2014.

Response for New Zealand Application No. 612035, filed Jun. 28, 2014.

Office Action for U.S. Appl. No. 13/484,213, dated May 7, 2013.

Office Action for U.S. Appl. No. 13/484,213, dated Jun. 25, 2013.

Notice of Allowance for 13/484,213, dated Oct. 1, 2013.

Office Action (Restriction Requirement) for U.S. Appl. No. 14/176,046, dated Oct. 3, 2014.

Office Action for U.S. Appl. No. 14/176,046, dated Dec. 29, 2014.

Office Action for U.S. Appl. No. 14/176,046, dated Jun. 2, 2015.

Examiners Answer for U.S. Appl. No. 14/176,046, dated Feb. 26, 2016.

Decision on Appeal for U.S. Appl. No. 14/176,046, dated Jul. 2, 2018.

Notice of Allowance for U.S. Appl. No. 14/176,046, dated Sep. 13, 2018.

Office Action for U.S. Appl. No. 14/054,879, dated Oct. 26, 2015.

Notice of Allowance for U.S. Appl. No. 14/054,879, dated Mar. 30, 2016.

(56) References Cited

OTHER PUBLICATIONS

Office Action for U.S. Appl. No. 15/162,613, dated Jan. 26, 2017.
Office Action for U.S. Appl. No. 15/162,613, dated Jun. 27, 2017.
Notice of Allowance for U.S. Appl. No. 15/162,613, dated Oct. 10, 2017.
Office Action (Restriction Requirement) for U.S. Appl. No. 15/870,858, dated Jul. 24, 2018.
Office Action for U.S. Appl. No. 15/870,858, dated Oct. 25, 2018.
Notice of Allowance for U.S. Appl. No. 15/870,858, dated Feb. 6, 2019.
Office Action for U.S. Appl. No. 16/443,741, dated Jul. 20, 2020.
Notice of Allowance for U.S. Appl. No. 16/443,741, dated Aug. 26, 2020.
Office Action for U.S. Appl. No. 16/844,692, dated May 13, 2012.
Notice of Allowance for U.S. Appl. No. 16/844,692, dated Jul. 7, 2020.
U.S. Appl. No. 13/484,213, filed May 30, 2012 U.S. Pat. No. 8,649,890.
U.S. Appl. No. 14/176,046, filed Feb. 8, 2014 U.S. Pat. No. 10,124,234.
U.S. Appl. No. 14/054,879, filed Oct. 16, 2013 U.S. Pat. No. 9,345,348.
U.S. Appl. No. 15/162,613, filed May 23, 2016 U.S. Pat. No. 9,889,340.
U.S. Appl. No. 15/870,858, filed Jan. 13, 2018 U.S. Pat. No. 10,322,314.
U.S. Appl. No. 16/443,741, filed Jun. 17, 2019.
U.S. Appl. No. 16/844,692, filed Apr. 9, 2020 U.S. Pat. No. 10,7922,537.
"A Revolution in Exercise Logbook Software" Available at https://web.archive.org/web/20100330075737/http:/www.zonefivesoftware.com/sporttracks/; Mar. 30, 2010 (2 pages).
App Picker "Running, Walking and Biking with Endomondo" Available at https://www.apppicker.com/apps/333210180/running-walking-and-biking-with-endomondo; Oct. 7, 2009 (3 pages).
Baker, Max "Phone + Endomondo + Google Earth = Geeks Workout" May 9, 2010 (3 pages).
BikeRadar "Fun is Fast: Peaksware Revamp TrainingPeaks WKO+" Jan. 12, 2010 (3 pages).
BusinessWre "MapMyFITNESS and Wahoo Fitness Integrate iMapMy Apps with ANT + to Provide Fitness Enthusiasts Heart Rate Data On-The-Go Using iPhone" Dec. 15, 2010 (2 pages).
Butcher, Mike "Map My Tracks: Live GPS Map Creation, and Sharing on the Way" TechCrunch; Feb. 18, 2009 (2 pages).
CNET "My Tracks (Android) Review: Google makes a Solid Multipurpose GPS Track" Date Unknown (4 pages).
Cohen, Peter "rubiTrack Workout Software Uses GPS Data" Macworld; Sep. 30, 2008 (4 pages).
DC Rainmaker "Garmin Edge 810 In-Depth Review" Jan. 7, 2013 (113 pages).
DC Rainmaker "Training Logs" Nov. 15, 2008 (14 pages).
DC Rainmaker "A Look at CompuTrainer ANT+ Integration via ctANT+" May 18, 2011 (27 pages).
DC Rainmaker "An Inside Look at Downloading FR310XT Workouts to the Web Without a Computer" Available at https://www.dcrainmaker.com/2011/05/inside-the-look-at-downloading-fr310xt.html; May 4, 2011 (55 pages).
DC Rainmaker "Behind the Scenes of Team HTC-Columbia and the Tour de France Live Tracker" Available at https://www.dcrainmaker.com/2010/07/behind-scenes-of-team-htc-columbia-and.htm.; Jul. 15, 2010 (17 pages).
DC Rainmaker "Checking Out the EZ-Trainer iPad ANT+ App" Available at https://www.dcrainmaker.com/2011/02/checking-out-ez-trainer-ipad-ant-app.html; Feb. 2, 2011 (29 pages).
DC Rainmaker "Hands on Review of the Sony Ericsson Xperia Active ANT+ Enabled Waterproof Phone" Available at https://www.dcrainmaker.com/2011/09/hands-on-review-of-sony-ericsson-experia.html; Sep. 12, 2011 (53 pages).

DC Rainmaker "My 2011 ANT+ Symposium Presentation" Available at https://www.dcrainmaker.com/2011/09/my-2011-ant-symposium-presentation.html; Sep. 30, 2011 (10 pages).
DC Rainmaker "Sport Tracks 3.0 Upgrade Review" Available at https://www.dcrainmaker/com/2010/09/sport-tracks-30-upgrade-review-html; Sep. 16, 2010 (25 pages).
DC Rainmaker "Sports Tracks in Depth—Ten Little Tidbits" Available at https://www.dcrainmaker.com/2009/12/sports-tracks-in-depth-ten-little.html; Dec. 1, 2009 (26 pages).
DC Rainmaker "Tip of the Day: Remembering to Retire Your Running Shoes" Available at https://www.dcrainmaker.com/2011/04/tip-of-the-day-rememering-to-retire-your.html; Apr. 29, 2011 (6 pages).
DC Rainmaker "Training Logs" Nov. 15, 2008 (17 pages).
Djailla's Blog "Testing the 'Joggy Coach' App for iPhone" Mar. 1, 2010 (7 pages).
Endomondo "FAQ Site Tour Tutorial" Available at https://web.archive.org/web/20100311005247/http/www.endomondo.com/help/sitetour; Mar. 11, 2010 (2 pages).
Endomondo "About US" Available at https://web.archive.org/web/20100315091123/http:/www.endomondo.com/about; Mar. 15, 2010 (2 pages).
FitCentric Technologies, Inc. "UltraCoach: Multi-Sport Fitness Data Management" Unknown Date (63 pages).
FitCentric Technologies, Inc. "NetAthlon: Motivation is the Key to Success" Available at https://web.archive.org/web/20020603181308/http:/www.fitcentric.com/na.htm; Jun. 3, 2002 (4 pages).
FitCentric Technologies, Inc. "Web Racing Requirements" Available at https://web.archive.org/web/20020604001525/http:/www.fitcentric.com/req.htm; Jun. 4, 2002 (2 Pages).
FitCenric Technologies, Inc. "UltraCoach Overview" Available at https://web.archive.org/web/20020604013714/http:/www.fitcentric.com/uc.htm; Jun. 4, 2002 (3 pages).
GameSpy "UltraCoach and NetAthlon Software Programs" Date Unknown (39 pages).
Golden Cheetah "Cycling Performance Software for Linux, Mac OS X, and Windows" Available at https://web.archive.org/web/20110510170446/http://goldencheetah.org.; May 10, 200 (1 page).
Golden Cheetah "Cycling Performance Software for Linux, Mac OS X, and Windows" Available at https://web.archive.org/web/20110811064924/http://goldencheetah.org/users-guide.html; Aug. 11, 2011 (5 pages).
Golijan, Rosa "Adidas miCoach Pacer Review: Like Nike+, Only Better" Gizmodo; Mar. 4, 2010 (11 pages).
Hays, David S. "2004 Running Log" Date Unknown (51 pages).
iClarified "Toolsfactory Releases rubiTrack 1.3" Available at https://www.iclarified.com/2562/toolsfactory-releases-rubitrack-13; Jan. 5, 2009 (11 pages).
iSmoothRun "Don't Worry About GPS Signal" Available at https://web.archive.org/web/20110926032658/http:/www.ismoothrun.com/features/; Sep. 26, 2011 (4 pages).
iSmoothRun "Run Further. Run Faster. Train Smarter. Introducing iSmoothRun" Aug. 20, 2011 (1 page).
Joggy Coach "Joggy Coach: The Ideal Partner for Your Running Sessions" Available at https://web.archive.org/wb/20100216202806/http:/www.joggycoach.com/home.html; Feb. 16, 2010 (1 page).
Joggy Coach "Joggy Coach—Running Jogging GPS Stopwatch" Available at https://www.deepaso.com/app/cn/343740663; Date Unknown (3 pages).
Larson, Peter "Review of SportTracks for Garmin Forerunner GPS Watches: Great Free Program for Downloading Garmin Data" Runblogger.com; Mar. 7, 2010 (8 pages).
Lau, Matthew B. "The Snap! Toolkit: A Model for Pluggable Monitoring" Massachusetts Institute of Technology; May 5, 2000 (60 pages).
Maker, Ray "Feedback by the Millions: What Athletes Really Want" DC Rainmaker; Unknown Date (19 pages).
Maker, Ray "The Athletes Digital Life" DC Rainmaker; Date Unknown (16 pages).
MapMyTracks "Real-Time GPS Tracking for Sports Enthusiasts—About My Tracks" available at https://web.archive.org/web/20080229111921/http:/www.mapmytracks.com/about-map-my-tracks; 2008 (3 pages).

(56) References Cited

OTHER PUBLICATIONS

MapMyTracks "Real-Time GPS Tracking for Sports Enthusiasts—Real-Time Event and Race Tracking from Map My Tracks" available at https://web.archive.org/web/20080329020214/http:/www.mapmytracks.com/event-race-tracking; Mar. 29, 2008 (2 pages).
MapMyTracks "Real-Time GPS Tracking for Sports Enthusiasts: Map My Tracks—Sign Up" available at https://web.archive.org/web/20100824002751/http:/www.mapmytracks,com/sign-up; Aug. 24, 2010 (1 page).
MapMyTracks "Real-Time GPS Tracking for Sports Enthusiasts and Sports Event Organisers" Feb. 17, 2010 (5 pages).
MapMyTracks "Real-Time GPS Tracking for Sports Enthusiasts: Frequently Asked Questions About Map My Tracks" Available at https://web.archive.org.web/20100824160937/http:/www.mapmytracks.com/help/faqs; Aug. 24, 2010 (2 pages).
MapMyTracks "Real-Time GPS Tracking for Sports Enthusiasts—Map My Tracks User Guide" Available at https:/web.archive.org/web/20100830081259/http:/www.mapmytracks.com/user-guide/getting-started/quick-start-guide, May 24, 2010 (2 pages).
MapMyTracks "Real-Time GPS Tracking for Sports Enthusiasts: Map My Tracks" Available at https://web.archive.org/web/20080311202545/http:/mapmytracks.com; Mar. 11, 2008 (4 pages).
MapMyTracks "Real-Time GPS Tracking for Sports Enthusiasts: Map My Tracks Mobile Screenshots" Available at https://web.archive.org/web/20080315224017/http:/www.mapmytracks.com/about/screenshots; Mar. 15, 2008 (7 pages).
MapMyTracks "Bol d'Or Mirabaud Extends GPS Tracking to the Whole Fleet Courtesy of Map My Tracks" May 10, 2020 (3 pages).
MapMyTracks "MMT Pro Sports Timing App" Available at https://web/archive.org/web/20100106133807/http:/www.mapmytracks.com/about/products/map-my-tracks-pro-sports-timing; Jan. 6, 2010 (2 pages).
MapMyTracks "Map My Tracks is the Easy Way to Accurately Track or Share in Real-Time, Your Location Over Land, Sea or Air Using Your Mobile Phone" Available at https://web.archive.org/web/20100525103032/http:/www.mapmytracks.com/about-map-my-tracks/; May 25, 2010 (2 pages).
MapMyTracks "MMT Mobile Phone Tracker" Available at https://web.archive.org/web/20100818032215/https:/www.mapmytracks.com/about/products.map-my-tracks-tracker/; Aug. 18, 2010 (2 pages).
MapMyTracks "Map My Tracks Becomes Official GPS Tracking Supplier for the Tour of Britain" Sep. 3, 2012 (4 pages).
MapMyTracks "Introducing Map My Tracks Mobile" Available at https://web.archive.org/web/20100211205133/https:/www.mapmytracks.com/blog/entry/introducing-map-my-tracks-mobile/; Jan. 2, 2009 (3 pages).
MapMyTracks "Map My Tracks Event Manager" Available at https://web.archive.org/web/20100923220353/http:/www.mapmytracks.com/about/products/map-my-tracks-event-management-system; Sep. 23, 2010 (2 pages).
MapMyTracks "Map My Tracks Products and Applications" Available at https://web.archive.org/web/20100818044011/http:/www.mapmytracks.com/about/products/; Aug. 18, 2010 (2 pages).
MapMyTracks "Real-Time GPS Tracking for Sports Enthusiasts—Blog" Available at https://web.archive.org/web/20080329030231/http:/www.mapmytracks.com/blog/entry/live-event-and-race-gps-tracking-from-map-my-tracks/; Mar. 29, 2008 (3 pages).
MapMyTracks "Introducing Map My Tracks Event Tracking at the Tour Down Under" Jan. 16, 2012 (4 pages).
Manninen, JP "RunKeeper's iPhone App Lets You Broadcast Your Morning Run to a Live Audience" Venture Beat; Mar. 26, 2010 (4 pages).
Micke-Midlife "Endomondo Running App Tells You Your KM Pace" Apr. 9, 2010 (6 pages).
Mueller, Joe "How to use Endomondo—GPS for Today" GPS for Today; Available at www.gpsfortoday.com/how-to-use-endomondo/; Feb. 22, 2012 (8 pages).
NetAthlon "NetAthlon 2XF for Cycling User Guide" RA Sports, LLC; 2010 (40 pages).
NetAthlon "NetAthlon 2XF for Running/Skiing User Guide" RA Sports LLC; 2010 (35 pages).
NetAthlon "NetAthlon 1.0 Even Edition" Available at https://web.archive.org/web/20101110235326/https:/riderunrow.com/products_eventedition.htm; Jan. 11, 2010 (2 pages).
NetAthlon "NetAthlon Products" Available at https://web.archive.org/web/20101208044646/http:/www.riderunrow.com:80/products_na2.html; Jan. 20, 2010 (3 pages).
NetAthlon "NetAthlon 1.0 Virtual Interactive Fitness Software" Available at https://web.archive.org/web/20100314012601/http:/www.riderunrow.com/products_na1.htm; Mar. 14, 2010 (2 pages).
NetAthlon "NetAthlon—WebRacing" Available at https://web.archive.org/web/20100830065459/http:/www.riderunrow.com/products_webracing.htm; Aug. 30, 2010 (3 pages).
NetAthlon "NetAthlon Compatible Fitness Equipments" Available at https://web.archive.org/web/20100223091841/http:/www.riderunrow.com/fitness_machines.htm; Feb. 23, 2010 (1 page).
NetAthlon "User Guides—NetAthlon 1.0 and 2.0, NetAthlon LAN, UltraCoach, Peak Sensor Kit" Available at https://web.archive.org/web/20100127013107/http:/www.riderunrow.com/userguides.htm; Jan. 27, 2010 (1 page).
Peak Training System "Turn Any Bike Trainer, Exercise Bike, Treadmill, or Rowing Machine into a Virtual Reality Experience for Home and Club Use" Available at https://web.archive.org/web/2010029225239/http:/www.riderunrow.com/products_sensors.htm; Oct. 29, 2010 (2 pages).
Peaksware, LLC "TrainingPeaks: Open iTunes to buy and download app" Available at https://web.archive.org/web/20110902080708/http:/itunes.apple.com/app/trainingpeaks/id408047715?mt=8; Sep. 2, 2011 (3 pages).
"Product Screen Shots" Available at https://web.archive.org/web/20100328070418/http:/www.zonefivesoftware.com/sporttracks/demo/screenshots-1.php; Mar. 28, 2010 (3 pages).
Redin, Maria "Marathon Man" MIT Media Laboratory et al.; Jun. 15, 1998 (57 pages).
Rubitrack "rubiTrack 2.2.1—Equipment Management and Tracking" Available at https://web.archive.org/web/20100404131634/http:/www.rubitrack.com/autoupdate/rn-2.2.1.html; Mar. 25, 2010 (1 page).
Rubitrack "rubiTrack 2.2.1—Equipment Management and Tracking" Available at https://web.archive.org/web/20100526145255/http:/www.rubitrack.com/autoupdate/rn-2.2.5.html; Apr. 22, 2010 (1 page).
Rubitrack "GPS Enabled Activity and Exercise journal for the Mac" Available at https://web.archive.org/web/20100511051150/http:/www.rubitrack.com:80/index.html; May 11, 2010 (2 pages).
Rubitrack "rubiTrack for iPhone 2.0" Available at https://web.archive.org/web/20100522135334/http:/www.rubitrack.com/iphone.html; May 22, 2010 (2 pages).
Rubitrack "The rubiTrack Forum" Available at https://web.archive.org/web/20100413191112/http:/www.rubitrack.com/forum/viewforum.php?f=2; Apr. 13, 2010 (5 pages).
Rubitrack "rubiTrack: Coming Soon: rubiTrack for iPhone" Available at https://web.archive.org/web/20081219055237/http:rubitrack.com/iphone.html; Dec. 10, 2008 (1 page).
Rubitrack "Frequently Asked Questions" Available at https://web.archive.org/web/20100403033805/http:/www.rubitrack.com/faq.html; Apr. 3, 2010 (3 pages).
RunKeeper "RunKepper is a "Nike+" for, Runners, Cyclists and More" Available at https://www.wired.com/2009/07/working-out-the-data-a-nike-for-cyclists/; Jul. 22, 2009 (10 pages).
RunKeeper Forum "Noob Question—What Do I Need for LiveTracking" Available at https://web.archive.org/web/20100509061626/http:runkepper.com/forum/viewtopic.php?f=5&t=4289; Apr. 29, 2010 (2 pages).
Sterling, Greg "Google "My Tracks" Uses Android GPS to Capture Outdoor Performance" Feb. 12, 2009 (7 pages).
Techman "Joggy Coach App for iPhone Review" Apr. 23, 2010 (5 pages).
Tinderhouse "OutFront: All Sport GPS Computer—Perform, Analyse & Share Rides, Runs and Other Outdoor Activities" iTunes Preview; Available at https://web.archive.org/web/20100726101118/http:/itunes.apple.com/gb/app/outfront/id347858530?mt=8; Jul. 26, 2010 (3 pages).

(56) References Cited

OTHER PUBLICATIONS

Tofel, Kevin C. "RunKeeper Live: Broadcast Your Exercise, Race Info in Real-Time" Gigaom; Mar. 19, 2010 (3 pages).
Tofel, Kevin C. "Mobile Tech Minutes—Hands on with Moblin v2.1" The GigaOM Network; Nov. 5, 2009 (6 pages).
TPCourtney "Gear's Thoughts: 2011 Customer Survey Results" Training Peaks GPS; Jun. 6, 2011 (5 pages).
Training Peaks: The Ultimate Training & Nutrition Software "Become a Part of the Community" https://web-archive.org/web/20100810185052/http:home.trainingpeaks.com/personal-edition/community-messageboards.aspx; Aug. 10, 2010 (1 page).
Training Peaks: The Ultimate Training & Nutrition Software "Maximize Your Training Time" available at https://web.archive.org/web/2010090206344/http:/home.trainingpeaks.com:80/personal-edition.schedule-training-and-plan-meals.aspx; Sep. 2, 2010 (1 page).
Training Peaks: The Ultimate Training & Nutrition Software "Track Changes in Your Fitness" Available at https://web.archive.org/web/20100726230716/http:/home.trainingpeaks.com/personal-edition/monitor-fitness-trends.aspx; Jul. 26, 2010 (1 page).
Training Peaks: The Ultimate Training & Nutrition Software "TrainingPeaks Personal Edition" Available at https://web.archive.org/web/20110204060617/http:home.trainingpeaks.com/personal-edition/training-log-and-food-diary.aspx; Feb. 4, 2011 (1 page).
Training Peak "Bike MS: TrainingPeaks" Date Unknown (4 pages).
Training Peaks: The Ultimate Training & Nutrition Software "Personal Edition Frequently Asked Questions" Available at https://web.archive.org/web/20100820051523/http:/support.trainingpeaks.com/personal-edition/personal-edition-faqs.aspx#Q2; Aug. 20, 2010 (6 pages).
Training Peaks: The Ultimate Training & Nutrition Software "TrainingPeaks Mobile" Available at https://web.archive.org/web/20100523220644/https:/support.trainingpeaks.com/trainingpeaks-mobile.aspx; May 23, 2010 (4 pages).
Training Peaks: The Ultimate Training & Nutrition Software "Monitor, Analyze and Plan Your Training with TrainingPeaks" Available at https://web.archive.org/web/20100813132719/https:/support.trainingpeaks.com/personal-edition/training-how-tos.aspx; Aug. 13, 2010 (2 pages).
Training Peaks "PedometerPro Step Counting Fitness for iPhone and Pod Touch" Available at https://web.archive.org/web/20110710123111/http:/home.trainingpeaks.com/mobile-apps/pedometer.pro.aspx; Jul. 10, 2011 (4 pages).
Training Peaks: The Ultimate Training & Nutrition Software "Training Peaks GPS: PGPS Fitness Tracking for iPhone 3G/3Gs/4" Available at https://web.archive.org/web/20110326041450/http:/home.trainingpeaks.com:80/mobile-apps/iphone-trainingpeaks-gps.aspx; Mar. 26, 2011 (6 pages).
Training Peaks: The Ultimate Training & Nutrition Software "Managing Equipment—Shoes & Bikes" Available at https://web.archive.org/web/20100817105800/http:/support.trainingpeaks.com/personal-edition/user-settings/equipment.aspx; Aug. 17, 2010 (2 pages).
Training Peaks "Training Peaks Professional Edition" Available at https://web.archive.org/web/20110405195753/http:/home.trainingpeaks.com/professional-edition/client-management-tools.aspx; Apr. 5, 2011 (1 page).
Training Peaks: The Ultimate Training & Nutrition Software "See Exactly What You Did" Available at https://web.archive.org/web/20100818232112/http://home.trainingpeaks.com/personal-edition/log-and-analyze-workouts.aspx; Aug. 18, 2010 (1 page).
Training Peaks "Training Peaks App: All Your Fitness Needs Just a Tap Away" Available at https://web.archive.org/web/20110710104052/http:/home.traninpeaks.com/mobile-apps.aspx; Jul. 10, 2011 (1 page).

Training Peaks "What Are You Training For?" Available at https://web.archive.org/web/20110524042227/http:/home.traininhpeaks.com; May 24, 2011 (3 pages).
Training Peaks: The Ultimate Training & Nutrition Software "Workout & Meal Details View" Available at https://web.archive.org/web/20100811062234/http:/support.trainingpeaks.com/personal-edition/detailed-view.aspx; Aug. 11, 2010 (2 pages).
Training Peaks: The Ultimate Training & Nutrition Software "TrainingPeaks.com Dashboard" Available at https://web.archive.org/web/20100726015956/http:/support.trainingpeaks.com/personal-edition/dashboard.aspx; Jul. 26, 2010 (1 page).
Training Peaks: The Ultimate Training & Nutrition Software "Compatible Devices and How to Use Them" Available at https://web.archive.org/web/20100504201609/http:/support.trainingpeaks.com.compatible-devices.aspx; May 4, 2010 (2 pages).
Training Peaks: The Ultimate Training & Nutrition Software "TrainingPeaks WKO+ Version 3.0" Available at https://web.archive.org/web/20110319013400/http:/home.trainingpeaks.com/wko-desktop-software/analysis-software-for-training-files.aspx; Mar. 19, 2011 (1 pages).
Training Peaks "TrainingPeaks Online Mobile" Available at https://web.archive.org/web/20110507064447/http:/support.trainingpeaks.com:80./trainingpeaks-online-mobile.aspx; May 7, 2011 (2 pages).
Training Peaks "Equipment Pod: The Equipment Pot is Standard for All Premium and Basic Account Subscribers" Available at https://web.archive.org/web/20100427022505/http:/support.trainingpeaks.com/pesonal-edition/pods/equipment-pod.aspx; Apr. 27, 2010 (2 pages).
Training Peaks "Coach Edition Frequently Asked Questions" Available at https://web.archive.org/web/20110629101049/http:/support.trainingpeaks.com/coach-edition-faqs.aspx; Jun. 29, 2011 (2 pages).
Training Peaks: The Ultimate Training & Nutrition Software "How to Add a Workout" Available at https://web.archive.org/web/20100811171539/http:/support.trainingpeaks.com/personal-edition/training-how-tos/how-to-add-a-workout.aspx: Aug. 11, 2010 (1 page).
Training Peaks: The Ultimate Training & Nutrition Software TrainingPeaks.com Spreadsheet: Available at https://web.archive.org/web/20100820034736/http:/support.trainingpeaks.com/personal-edition/spreadsheet.aspx; Aug. 20, 2010 (1 page).
UltraCoach "UltraCoach 3.0 Athletic Training Software v 3.0" Available at https://web.archive.org/web/20100113012221/https:/www.eiderunrow.com:80/peoducts_uc_htm; Jan. 13, 2010 (3 pages).
UltraCoach "Heart Rate Monitors Compatibility" Available at https://web.archive.org/web/20100404062637/http:/www.riderunrow.com/compatibility_hrm.htm; Apr. 4, 2010 (1 page).
Van Grove, Jennifer "RunKeeper's Genius Use of GPS for Tracking Your Runs" Feb. 16, 2009 (2 pages).
Webster, Scott "My Tracks" App Review: Google My Tracks; Feb. 15. 2009 (5 pages).
Weightmania.com—Fitness and Nutrition Software "Weightmania Pro Online" Available at https://web/archove.org/web/20100213095231/http:/www.weightmania.com/wmonlinefacts.htm; Feb. 13, 2010 (8 pages).
Weightmania.com "Weightmania Pro User Guide for Windows XP and Vista Users" Edward A Greenwood, Inc.; 2009 (107 pages).
Weightmania.com "Weightmania Pro: Fitness & Nutrition Software That Tracks Over 100 Things" Available at https://web.archive.org/web/2010020900353/http:/www.weightmania.com; Feb. 9, 2010 (3 pages).
Zee "RunKeeper Live Lets You Track Someone (Running) in Real Time, Online," APPS; Mar. 17, 2010 (10 pages).
U.S. Appl. No. 17/093,864, filed Nov. 10, 2020, Martin.

* cited by examiner

| Racing Calendar | | | | |
|---|---|---|---|---|
| Select | Date | Event | Location | Contact |
| ☐ | 6/4/11 | 5k | Zuma | Todd |
| ☑ | 6/4/11 | 10k | Sydney | Natasha |
| ☐ | 6/4/11 | 5k | LA | Race Management Inc. |

FIG.2B

| Training Plan | | | |
|---|---|---|---|
| Date | Activity | Route | Workout |
| 6/12/11 | Running | The tan | Interval |
| 6/19/11 | Swimming | Palisades pool | 5x100m Free |

FIG.3

| June | | | | | | |
|---|---|---|---|---|---|---|
| S | M | T | W | Th | F | S |
|  |  |  | 1 | 2 | 3 | 4 Sydney 10k |
| 5 | 6 | 7 | 8 | 9 | 10 | 11 |
| 12 | 13 | 14 | 15 | 16 | 17 | 18 |
| 19 | 20 | 21 | 22 | 23 | 24 | 25 |

"Interval Workout" → 12

SYSTEM AND METHOD FOR PROVIDING A COACH WITH LIVE TRAINING DATA OF AN ATHLETE AS THE ATHLETE IS PERFORMING A CYCLING WORKOUT

CROSS-REFERENCE TO RELATED APPLICATIONS

This Application is a continuation of U.S. application Ser. No. 16/844,692, filed Apr. 9, 2020, now U.S. Pat. No. 10,792,537, which is a continuation of U.S. application Ser. No. 16/443,741, filed Jun. 17, 2019, which is a continuation of U.S. application Ser. No. 15/870,858, filed Jan. 13, 2018, now U.S. Pat. No. 10,322,314, which is a continuation of U.S. application Ser. No. 15/162,613, filed May 23, 2016 now U.S. Pat. No. 9,889,340, which is a continuation of U.S. application Ser. No. 14/054,879, filed Oct. 16, 2013, now U.S. Pat. No. 9,345,948, which claims the benefit of U.S. Provisional Application No. 61/715,847, filed Oct. 19, 2012, the entire contents of each being incorporated by reference herein.

FIELD OF THE INVENTION

The present invention relates to improvements in a system for storing training data entered by an athlete, associating information with the athlete that is related to the athlete's participation in training and/or racing activities, and generating a profile specific to the athlete for use by the athlete and/or a coach.

BACKGROUND OF THE INVENTION

Athletes training for a competition usually enlist the assistance of a coach to help them prepare for an upcoming competition, or to enhance their personal fitness. Often, the athlete becomes attached to a particular coach, but then has to move to a different city for any number of reasons. This can disrupt the athlete's training, leading to a loss of fitness, and a loss of personal time in trying to find a replacement coach in the new area in which the athlete finds themselves. The present invention in one or more preferred embodiments seeks to provide an athlete with the ability to maintain their current relationship with a preferred coach regardless of their physical location.

SUMMARY

The present invention in one preferred aspect is directed to a web-based platform tailored to providing access to information regarding athletic or sporting events and personal training information. The system may include an activity calendar, which is personalizable, a training log, a media portal containing photos of a participant in an event, and a rankings generator configured to rank a user against other users within given set of parameters.

As used herein, "configured" includes creating, changing, or modifying a program on a computer or network of computers so that the computer or network of computers behave according to a set of instructions. The programming to accomplish the various embodiments described herein will be apparent to a person of ordinary skill in the art after reviewing the present specification, and for simplicity, is not detailed herein.

It will be appreciated that in one or more embodiments, the system may include one or more work stations at a back end for use by a platform operator, one or more local client computers for access by users, and a communications network that facilitates communication between the platform, the work stations at the back end, and the client computers. Preferably, the work stations and client computers will include a display and means for entering information, such as a keyboard and/or voice activated data entry. Means for accessing the platform by users may include, but is not limited to personal computers and mobile devices such as tablets and smartphones, and other user devices capable of communicating over a communications network such as the Internet.

In one preferred aspect, the present invention is directed to a web-based platform for personalizing a training regimen of an athlete. The system preferably includes a training log server configured to maintain a plurality athlete profiles, each athlete profile including a training record having a plurality of fields that each correspond to an aspect of a workout in which the athlete participated, one of the fields corresponding to a distance aspect of the workout, another of the fields corresponding to a time aspect of the workout. The system preferably further includes a processor programmed to receive workout data supplied by the athlete and update the training record with the workout data, the workout data including both a distance aspect and a time aspect. The processor is configured to permit the athlete to grant access to the training record to a coach so that the coach may log onto the platform and view the training record. The processor is further configured to receive a training plan from the coach and associate the training plan with the athlete profile so that the athlete may view the training plan.

The processor may be programmed to cumulatively track at least one aspect of the athlete's workouts. The processor may be programmed to generate a calendar incorporating at least a portion of the training plan. The calendar may be presented as a monthly calendar. The processor may be programmed to send a message to the athlete once the training plan has been uploaded to the platform and associated with the athlete profile. The processor may be programmed to send a message to the coach once the athlete updates their training record. The processor may be programmed to permit the athlete to selectively restrict access by the coach to portions of the training record.

The platform further preferably includes a media portal configured to receive media from at least one of the athlete and the coach and associate the media with the athlete profile.

In another preferred aspect, the present invention is directed to a method for personalizing a training regimen of an athlete using a computer web-based platform, the platform including a processor and a training log server configured to maintain a plurality of athlete profiles. The method preferably includes creating an athlete profile on the training log server, the athlete profile including a training record having a plurality predefined fields, at least one of the fields corresponding to a distance aspect of an athlete's workout, at least another of the fields corresponding to a time aspect of the athlete's workout; receiving, at the platform, workout data from the athlete, the workout data including a distance aspect and a time aspect; updating the training record of the athlete profile by associating each aspect of the workout data with the corresponding field in a training record; permitting a coach to log onto the platform and view the athlete profile; and uploading a training plan from the coach to the platform and associating the training plan with the athlete profile.

The updating of the training record preferably includes calculating a cumulative training distance for a selected interval of time using the distance aspect of the workout data from the athlete. The method preferably further includes generating a calendar and populating the calendar with portions of the training plan. The method further preferably includes sending a message to the coach after the training record has been updated. The method further preferably includes sending a message to the athlete after the training plan has been uploaded to the platform and associated with the athlete profile. The method further preferably includes comparing the workout data for a given day with a planned workout forming part of the training plan and determining whether the athlete completed the workout as planned. The method further preferably includes generating a graphical representation comparing the athlete's actual workout to the planned workout. The workout data preferably includes data identifying a training route. The workout data preferably includes an aspect identifying a category of workout activity.

The present disclosure in another preferred aspect sets forth a system and method for transferring an athlete's training data from a bike computer to an online training log associated with the athlete. The system includes a bike computer mountable on a bike ridden by the athlete, the bike computer being configured to store training data accumulated during the course of a training session, the bike computer including a wireless transceiver configured for peer-to-peer communication. The system also includes a mobile communications device having a processor and a wireless communications transceiver, the processor being configured to receive the training data from the bike computer and format the training data for transfer to the athlete's online training log. The system also includes a web-based platform including a processor configured to receive the training data from the mobile communications device and store the training data in a training log server, the training log server having a plurality of athlete profiles, at least one of which corresponds to the athlete uploading the training data.

The wireless communications transceiver of the bike computer may utilize Wi-Fi Direct. The wireless communications transceiver of the bike computer may utilize Bluetooth. The mobile communications device may be paired with the bike computer. The mobile communications device may be a smart phone. The mobile communications device may be a tablet. The processor of the mobile communications device may be programmed to display the formatted training data on a display of the mobile communications device. The bike computer may be programmed to send a discovery message to the mobile communications device and automatically transfer the training data after a communications link has been established with the mobile communications device. The bike computer may be configured to establish a peer-to-peer communications link with more than one mobile communications device. The training data transferred to the mobile communications device may include GPS-based data.

The present disclosure in an additional preferred aspect sets forth a method for updating an online training log of a user. The method includes establishing a peer-to-peer communications link between a mobile training computer and a mobile communications device, the mobile training computer being sized and configured to be mounted on the user's bike; transferring training data stored on the mobile training computer to the mobile communications device using the peer-to-peer communications link; formatting the training data for transfer from the mobile communications device to a web-based platform; and uploading the formatted training data to the web-based platform to update the online training log of the user.

The mobile training computer may be a bike computer. The peer-to-peer communications link may be established using Wi-Fi Direct. The peer-to-peer communications link may be established using Bluetooth. The training data may be uploaded to the online training log without a USB interface. The training data may be transferred automatically to the mobile communications device once the peer-to-peer communications link is established.

The present disclosure in further preferred aspect sets forth a system for transferring an athlete's training data from a bike computer to an online training log associated with the athlete. The system includes a bike computer mountable on a bike ridden by the athlete, the bike computer being configured to store training data accumulated during the course of a training session, the bike computer including a wireless communications means for transmitting the training data; a mobile communications device having a processor and a wireless communications transceiver, the processor being configured to receive the training data from the bike computer and format the training data for transfer to the athlete's online training log; and a web-based platform including a processor configured to receive the training data from the mobile communications device and store the training data in a training log server, the training log server having a plurality of athlete profiles, at least one of which corresponds to the athlete uploading the training data.

The present disclosure in an additional preferred aspect sets forth a bike computer for collecting and transmitting an athlete's training data accumulated during a training session. The bike computer includes at least one sensor for measuring data associated with a parameter of the athlete's training session; a processor configured to collect the training data from the at least one sensor; a memory for storing the training data collected by the processor; and a wireless communications means for transmitting the training data to a training log.

The bike computer may include a mount configured to detachably secure the bike computer to a bike. The at least one sensor may include a cadence sensor. The at least one sensor may include a heart rate sensor.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE DRAWINGS

Reference will now be made in detail to the present preferred embodiments of the invention, examples of which are illustrated in the accompanying drawings.

Figure 1:
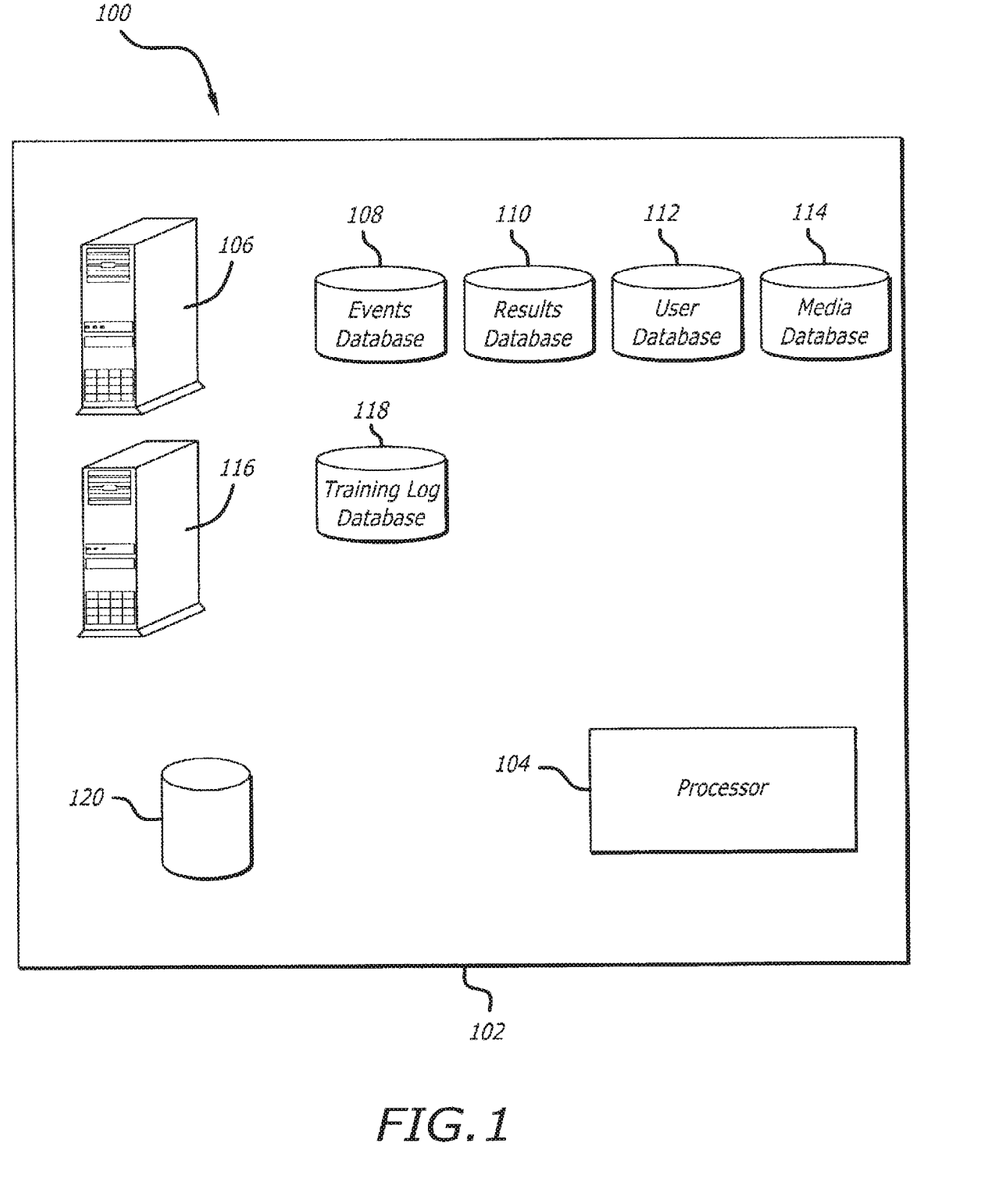
FIG. 1 is a diagram of system components in accordance with a preferred embodiment of the present invention.

FIG. 1 shows a preferred embodiment of a system 100 that includes a computer web-based platform 102 for preferably providing a user with access to an array of information regarding upcoming event information, event results, training plans and workouts, rankings information and media pertinent to the user's participation in a given event. Platform 102 preferably includes a processor 104, a database server 106 for maintaining an events database 108 that includes a listing of athletic events, a results database 110 that includes results of athletic competitions, a user database 112 that includes records of registered users, a media database 114, a training log server 116, a training log database 118, and a rankings generator 120. The preferred components of platform 102 and their interaction with each other are described further below.

Platform 102 is preferably a computer web-based system accessible by content providers and users. Content providers are preferably individuals or entities that upload or otherwise provide content or data to the platform relating to one or more athletic events or training activities. Content may include, but is not limited to results from athletic competitions, training plans and workouts supplied by a third party such as a coach, and media content such as photographs or video from third party providers. As used herein, a third party is a person or business entity that provides content on a commercial basis. Athletic events may include, but are not limited to running races, bike races, swim meets, triathlons, duathlons and other competitions pitting an individual or team against other individuals or teams. Users are preferably individuals or entities desiring access to the content provided by the content providers. Such users may include an individual interested in an upcoming event, a race result, a training plan or workout, and/or media pertaining to an event. Users may also include individuals such as athletes who supply data to the platform pertaining to their training in order to generate a training log, or coaches who supply or upload a training plan to the platform for purposes of coaching an athlete. In the examples that follow, the platform will be described for use with athletic events and activities relating to running, swimming, biking, triathlons and duathlons. It will be appreciated that the platform may be modified for other athletic events or activities as desired.

Platform 102 preferably includes multiple features accessible by content suppliers and users. For example only, platform 102 preferably includes an activity calendar 122, a results page, a training log 124, a rankings generator 120 and a media portal. To facilitate access to these and other features, database server 106 preferably maintains multiple databases of information. It will be appreciated that information may be stored in a cloud as an alternative to a database, or in addition to a database.

Event information for activity calendar 122 is preferably maintained in event database 108. Database 108 preferably includes data for each event. Such data may include, but is not limited to category of event (e.g., running, biking, swimming, triathlon), sub-category of event (e.g., for running, 5K, 10K, half-marathon, etc.), date and time, location, contact information and registration details, which may include a link to a site where a user may register for the event.

Information for the results page is preferably maintained in results database 110. Database 110 preferably includes records of results for specified events. Such records may be organized by event name, event category, event sub-category, date, geographic area, and/or event organizer or sub-contractor. Each record preferably contains the results of all participants who complete the competition. Such results may be organized by gender, over-all placing, placing within a predetermined age group, and/or geographic area (e.g. residence of a participant).

Information relating to user access is preferably maintained in user database 112. Database 112 preferably includes records of registered users. Each record preferably includes a record identifier; personal details of the user, such as name, address, gender and age; and access level, for example, cost-free access or subscription level access. Database 112 is useful for when a user accesses the platform and desires to access particular information which may be restricted depending upon the level of access of the user.

To facilitate access to the platform features, platform 102 preferably includes a processor 104 programmed to determine a content supplier or user's access to the platform. Access to platform 102 is preferably determined by whether an individual or entity is a platform operator, content supplier and/or a user. A platform operator has access to the entire platform. On the supply side of the platform, a content supplier may have access to create a record relating to an athletic event for listing in the activity calendar. A content supplier may also have access to upload event data such as race results, training plans which may include workouts, or media information such as photographs of a participant. As used herein, a workout is an activity where the user or athlete physically exerts themselves for the purpose of maintaining or improving their health or fitness.

On the consumer side of the platform, a user may have several levels of access. For example only, a user may have unrestricted access to some features of platform 102, such as the activity calendar. Other features of the platform may be configured for restricted access, which require a user to register with the platform by providing log-in details, for example, a user name and password. The log-in details are preferably stored in user database 112 and assigned a record identifier. Additional features of platform 102 may be configured for access only by users who are subscribers, i.e., pay a fee for access. Examples of restricted access features may include results data and/or media data. Examples of subscription-only features may include rankings data. Subscribers may be given access to all features of platform 102, while registered users may be given access only to unrestricted features and restricted features that are not subscriber-only features. It will be appreciated that the levels of access may be varied from feature to feature as desired.

Processor 104 is preferably configured to receive a request for access by a user and determine whether the access is restricted. If access is restricted, Processor 104 preferably requests the user to log in, or create a login if the user is a new user. Once processor 104 has determined that the user is a registered user (i.e., the user has provided or created a correct login), the registered user is granted access to the restricted access features of platform 102. If the feature requires a subscription-only access, processor 104 will grant access to the user upon a determination that the user is a subscriber. Additionally, processor 104 may offer the registered user an opportunity to become a subscriber if the registered user attempts to access a subscription-only feature and is not a subscriber.

Figure 2A:
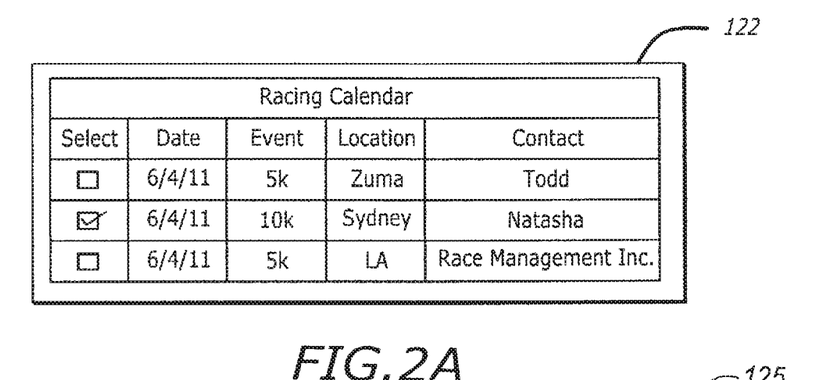
FIG. 2A is a preferred embodiment of a graphical user interface with fields for events for use in generating an activity calendar.
Figure 2B:
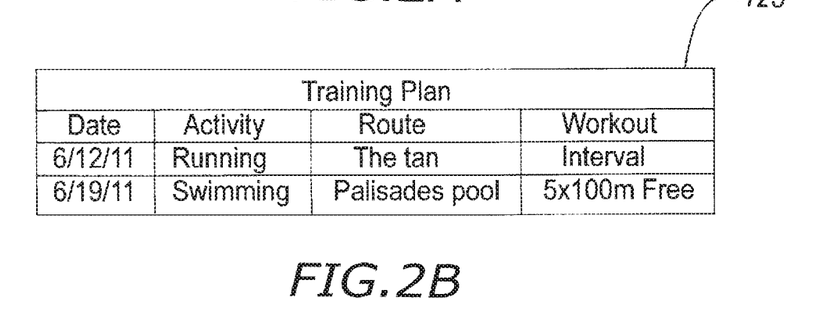
FIG. 2B is a preferred embodiment of a graphical user interface with fields for portions of a training plan for use in generating an activity calendar.
Figure 3:
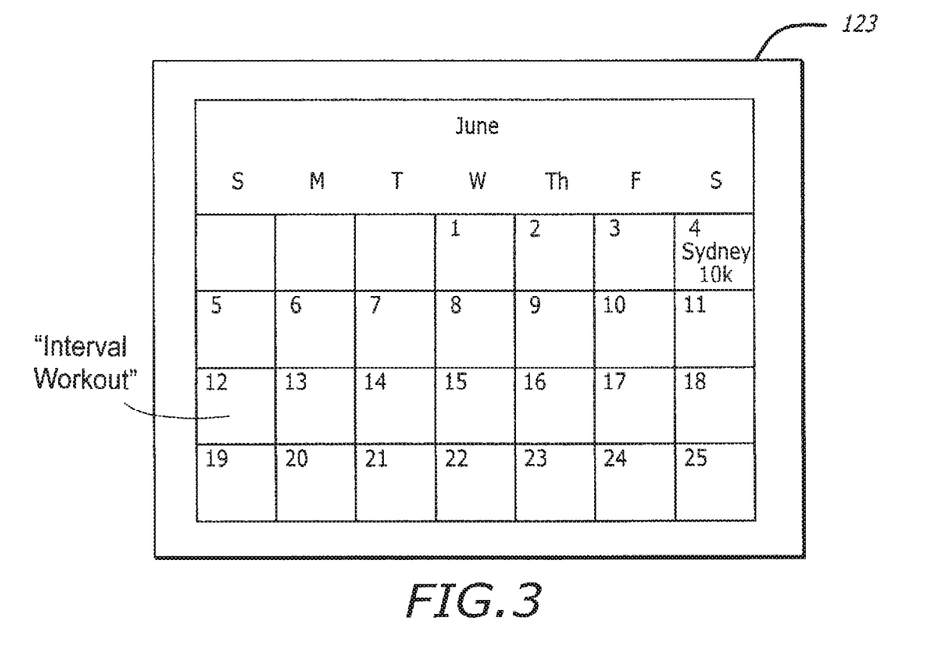
FIG. 3 is a front view of the activity calendar generated by the graphical user interfaces of FIGS. 2A and 2B.

Referring to FIGS. 1 to 3, platform 102 preferably includes an activity calendar 122 as one of its features. Processor 104 preferably is programmed to use information stored in events database 108 and/or training log database 118 to generate a graphical user interface listing athletic events and training activities. The athletic events are preferably organized by event category, sub-category, date, event title, location and contact information. The training activities are preferably organized by activity type (e.g., running, swimming, cycling, weight training), workout type (e.g. interval workout, long distance run or ride, swim sets), and training venue and/or route.

The activity calendar is preferably personalizable, i.e., a user may select desired events and organize the listing to include only the selected events. For example only, as shown in FIG. 2A, the activity calendar includes a means for selecting desired events, which in this example, includes a column of boxes, each box corresponding to a listed event, which the user may select by clicking on the box. Upon completing the desired selections, the user may instruct processor 104 to generate a calendar view 123 showing the selected events in a calendar format, such as shown in FIG. 3. The activity calendar may send automated reminders to registered users of upcoming selected events. Such reminders may include one or more links to permit the user to access an event website or register for selected event. Calendar view 123 is preferably configured to be updated with additional or replacement desired events. Events listed in the activity calendar and/or shown in the calendar view may include links to permit the user to access an event website or register for selected event.

The activity calendar preferably includes activities from a training plan uploaded to platform 102. For example, referring to FIG. 2B, data from selected fields in training plan record 125 is used to populate the activity calendar. Processor 104 may then generate calendar view 123 showing one or more workouts from training plan record 125.

Figure 4:
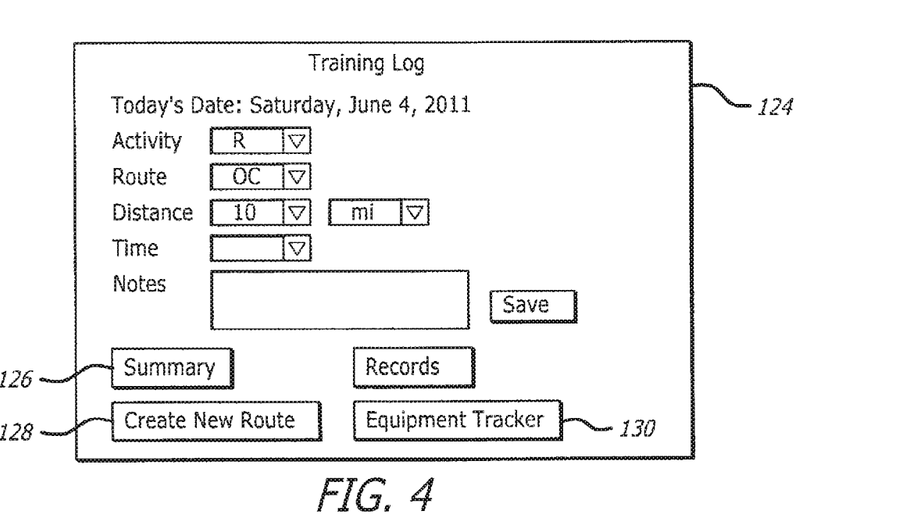
FIG. 4 is a preferred embodiment of a graphical user interface for use in generating a personal training log.

Referring to FIGS. 1 and 4, platform 102 preferably includes a training log 124 as one of its features. Training log 124 is preferably maintained by training log server 116 and includes a plurality of training records preferably stored at training log database 118. Processor 104 preferably is programmed to generate a graphical user interface having a plurality of fields and functions. The functions preferably include a "Summary" function 126 for summarizing training and/or racing data, a "Records" function for tracking a user's best performance data and an "Equipment Tracker" 130 for tracking the wear of various equipment used by the user. Each of these functions is described in greater detail below.

In order to optimize use of one or more of the functions, a user must enter data into the platform. As shown in FIG. 4, fields may be provided for date and activity in the training record. The date field may be automatically updated with the current date using the user's computer or mobile device. The activity field may be filled in or selected by the user from a predefined listing of activities, for example, running, swimming, biking, weight training, other, or racing. Each activity may be listed by its full name, or may be abbreviated to a single code (e.g., "R" for running, "B" for biking, etc.). A user may select from a menu the activity name or code for entry into the activity field. Once the user enters or selects the activity name or code, processor 104 generates additional fields for the user to fill in. The additional fields are preferably optimized for the particular activity selected. For example only, if running is the selected activity, the fields generated preferably include "Route," "Distance," "Time" and "Notes" as shown in FIG. 4.

The "Route" field may be an open field in which the user may enter a description of the training route, or may be configured to receive a route name or code corresponding to a route which the user previously described and stored, for example, using a "create new route" feature 128 described in greater detail below. For example, a user may describe and store a training route corresponding to the user's run along the ocean, and associate the route with a route name or code "OR." When the user subsequently enters information into the route field, the user may simply enter or select "OR" and the route information will be associated with the particular training log record being created. The "Distance" field preferably relates to the total distance the user traveled during the training activity. The "Distance" field may be automatically filled upon selection or entry of the route title or code, or modified independently of the route field. The "Time" field corresponds to the user's total training time for that activity. The "Notes" field is an open field which the user may enter notes regarding the training activity. Other fields may be added, for example, a heart rate field, a difficulty rating field, and/or a weather field.

For a swimming activity, processor 104 may generate fields relating to location, distance, time, notes and whether a wetsuit was used. For a biking activity, processor 104 may generate fields relating to route, distance, time, maximum speed, average speed, power and heart rate. As with the running activity, the "Route" field may be automatically filled upon entry or selection of the route name or code, or modified independently of the route field.

For the racing activity, processor 104 is preferably configured to generate fields relating to event category (e.g., running, biking, swimming, triathlon, duathlon, etc.), event sub-category and/or distance, splits, finish time, placing (over-all and age group) and notes. It will be appreciated that the number and type of activities may be varied as desired. Further, the number and type of fields may be modified as desired.

Figure 5:
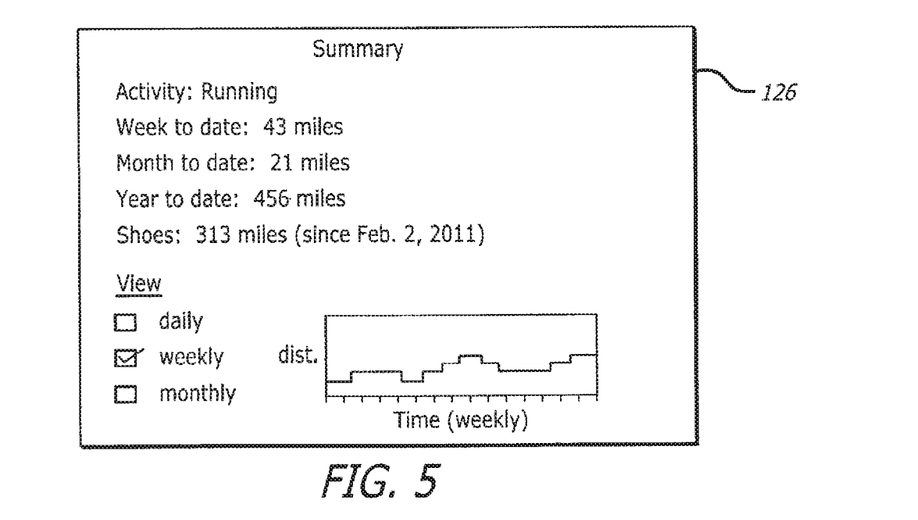
FIG. 5 is a preferred embodiment of a graphical user interface for use in generating a summary portion of the personal training log of FIG. 4.

Referring to FIGS. 4 and 5, the graphical user interface for training log 124 preferably includes a "Summary" function 126. Summary function 126 preferably automatically tracks and updates the user's data. In order to facilitate tracking of the user's data, the data stored for each field in database 118 is associated with a code, which processor 104 uses to maintain a running tally depending upon the type of code. Preferably summary function 126 is organized into racing activities and training activities.

Using running and biking as examples of training activities, processor 104 preferably updates a running tally for distance and time with each instance a new running or biking record is added to the user's training log. The running tally may be configured for one or more predetermined time periods. For example only, a running tally may be configured for weekly, monthly, annual, week-to-date, month-to-date and/or year-to-date for distance and/or time per an activity.

For example only, if a user desires to learn what their year-to-date distance is for biking, the user may select the "Summary" function and select a "Training Activities" function. The "Training Activities" function preferably generates an activity field. Selecting the activity name or entering the activity code into the field preferably generates a summary specific to the activity. For example, with running and biking activities, a training information field and a time period field will be generated. The user may then have the option of selecting one or more types of training information (e.g., distance and training time) for a selected time period (e.g., weekly, monthly, year-to-date, etc.). Upon making the selections, processor 104 generates a summary using the selection criteria entered by the user. The summary is preferably in a list form and preferably includes a graphical representation of the summary such as shown in FIG. 5.

Referring to FIG. 4, the training log preferably is configured with a "Records" function. The "Records" function preferably tracks a user's best performance data for a particular category of activity, for example, training and/or racing. For a training activity, the "Records" function, through processor 104 and training log database 118, stores the user's best performance record for a given activity. For example, for a training run where a user runs the "OC" route multiple times, each time the "OC" route is run by the user, the training time is entered by the user and processor 104 compares the newly entered time with prior times associated with the "OC" route. If a newly entered time for the "OC" route is less than any of the times currently of record for the "OC" route, the best time for the "OC" route is updated with the new best time and the date that the best time occurred.

If a user wishes to see what their best time is for a particular route, they may choose the running activity on a pull-down menu labelled "route." The pull-down menu will preferably be populated with the routes created from a "create new route" option 128, described in further detail below. When the user chooses a route from the pull-down menu, the records function will display the best time for that route and the date recorded for that time.

Similar best performance records may be maintained for times for other activities such as biking and swimming. Best performance records may be customized and maintained depending upon the training activity. For example, for running, biking and swimming, separate best performance records are preferably maintained for fastest time and longest distance. For biking in particular, best performance records are preferably additionally maintained for best average speed and best maximum speed. For swimming, best times may be recorded for set training distances.

If the category of activity relates to racing, the "Records" function is preferably configured to compare and update a user's best performance for a given race activity (e.g., running, biking, swimming, triathlon, etc.), sub-category and/or distance, splits, finish time, placing (over-all and age group) using methodology similar to that described above in relation to the training activity best records, but modified for the race environment. Examples of sub-categories of races for running include 5K, 10K, half-marathon, marathon, trailing running and track. Examples of races for cycling include road, track, cyclo-cross, mountain and BMX. Examples of sub-categories for races for swimming include open water and pool. Examples of sub-categories of races for multi-sport include triathlon (sprint, international, half-iron distance, iron distance), duathlon (sprint, international, long-distance), aquathon, aquabike, and off-road.

A running tally on placings is preferably maintained. Placings may be maintained for over-all placing in a competition, placing within an age group (typically 5-year increments commencing from age 20), a "best placing percentage," and career wins. The "Records" function is preferably configured to determine the "best" placings of the user within a given race. For example, if a user places $150^{th}$ over-all out of a running race of 1,500 participants, the placing is preferably recorded as being in the top 10%. A subsequent placing of $100^{th}$ out of 2,000 participants is preferably recorded as being in the top 5% and designated as the new best race placing. Similar place-tracking may be maintained within age groups. For career wins, the records function may track the number of first place wins over the span of their athletic career. The records function may also track age-group wins (i.e., the number of times the user wins their age-group).

Figure 6:
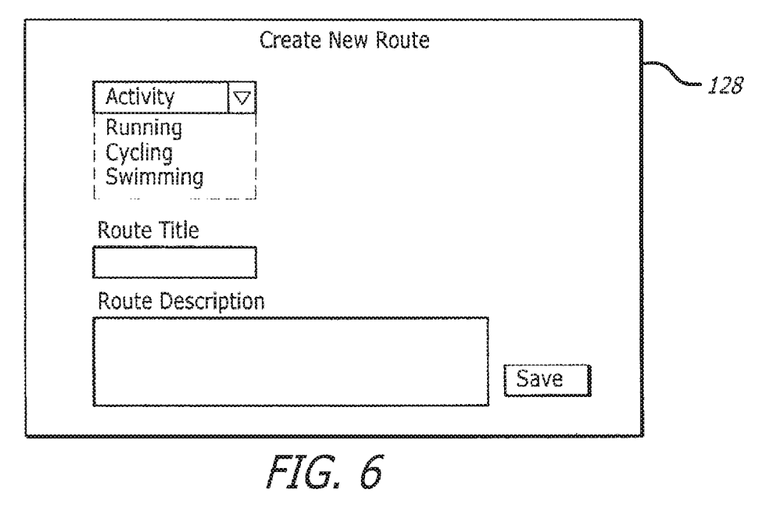
FIG. 6 is a preferred embodiment of a graphical user interface for use in creating a new route portion of the personal training log of FIG. 4.

Referring to FIGS. 4 and 6, platform 102 is preferably configured so that the user may create and record a route which may be used to later associate training data. Accessing link 128 will generate fields for the user to enter information pertaining to the route. A pull-down menu of activities such as running, cycling and swimming may permit the user to select an activity. Preferably, there will be two fields where the user enters information: a first field for entry of a route title or code, and a second one for entry of a route description. Once a route has been created and saved under the user-defined title or code, it will preferably be in a list of routes which will appear in the pull-down menu for the training log entries when entering training information.

Figure 7:
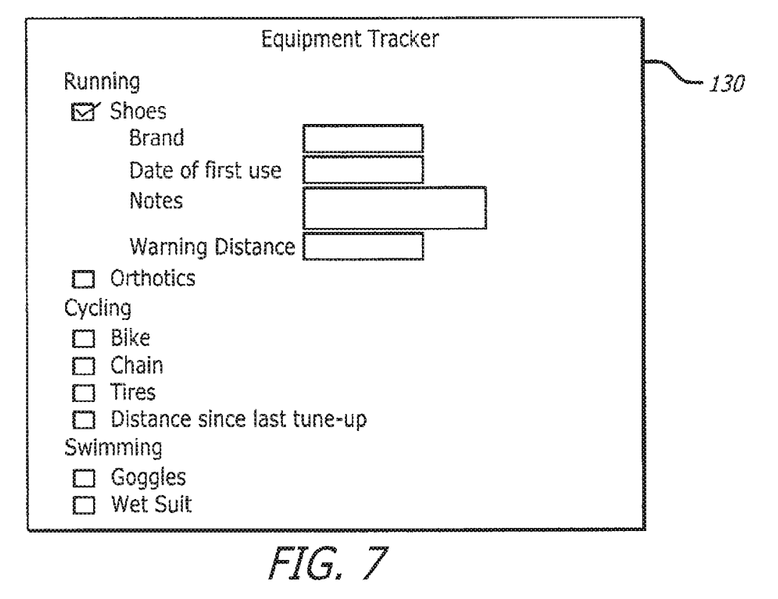
FIG. 7 is a preferred embodiment of a graphical user interface for use in generating an equipment tracker portion of the personal training log of FIG. 4.

Referring to FIGS. 4 and 7, the training log is preferably configured with an "Equipment Tracker" function 130. Equipment tracker function 130 tracks usage of various equipment used by the user during training and/or racing activities. For example, for running, the equipment tracker function 130 is preferably configured to track usage of running shoes and/or orthotics. For shoes, fields for brand, date of first use, notes, and warning distance may be filled by the user. This feature will track distance according to the distance logged when the user enters a distance for their run based on the dated entered in the date of first use field. The warning distance feature will cause a warning message to appear next time the user logs into their training log. The warning message will appear when the tally for the distance matches the warning distance value entered by the user. If desired, the warning message may be electronically communicated over a network to the user, for example, by e-mail or texting. For orthotics, fields will preferably be available for date of first use, notes and warning distance.

For biking, the equipment tracker function 130 is preferably configured to track usage of one or more of a bike, a chain, a pair of tires, distance traveled since the last tune-up of the bike, cassette and odometer batteries. For the bike, fields will preferably be available for brand, date of first use, and notes. This feature will track distance according to the distance logged when the user enters a distance for their cycling based on the date entered in the date of first use field. For the chain, fields will preferably be available for date of first use, notes and warning distance. For tires, fields will preferably be available for date of first use, notes, warning distance. The tires category may be sub-divided into racing and training. For distance since last tune-up, fields will preferably be available for date of tune-up, notes and warning distance. This feature will track distance according to the distance logged when the user enters a distance for their cycling based on the date entered in the date of tune-up field. For the cassette, fields will preferably be available for date of first use and notes. For odometer batteries, fields will preferably be available for date of first use and notes.

For swimming, equipment tracker function 130 is preferably configured to track usage of a pair of swimming goggles, wetsuit and swimsuit. Usage may be based on distance, time or a combination thereof. For goggles, fields will preferably be available for brand, date of first use and notes. This feature will track distance according to the distance logged when the user enters a distance for their swimming based on the date entered in the date of first use field. For wetsuit, dates will preferably be available for brand, date of first use and notes. This feature will track distance according to the distance logged when the user enters a distance for their swimming based on the date entered in the date of first use field and the user checks the box for "wetsuit used" option appearing on either the swim training or swim racing (open water) screen. For swimsuit, fields will preferably be available for brand, date of first use and notes.

It will be appreciated that programmed functions of the training log may be varied as desired. One or more of the functions described above may be omitted, or additional functions may be programmed into the training log. Moreover, though described in relation to running, swimming, biking and triathlons, it will be appreciated that the training log may be adapted for other activities, such as a training gateway described below.

In another preferred aspect of the present invention, platform 102 is preferably configured to function as a training gateway or nexus between an athlete and a coach. In order to maintain or improve fitness and athletic performance, athletes often associate themselves with a coach. Sometimes the coach is located at a remote location that renders it impractical for the athlete to attend a coaching session in person. Nonetheless, the athlete may obtain the benefit of a workout program generated by the coach by utilizing platform 102 as a training gateway.

To facilitate implementation of a training plan between a coach and an athlete, platform 102 may be configured to maintain an athlete profile that combines portions of the user information stored at user database 112 and training records populated by use of training log 124.

Referring to FIG. 1, trailing log server 116 is preferably configured to maintain a plurality of athlete profiles. Each athlete profile preferably includes personal information such as that stored in user database 112 (described above), and a training record having a plurality of fields that each correspond to an aspect of a workout in which the athlete participated. The training records are preferably stored in training log database 118 and preferably populated such as described above with respect to training log 124. The athlete profile is preferably configured to receive a training plan uploaded by a third party such as a coach. The athlete associated with the athlete profile has preferably preselected the coach and/or training plan, and either uploaded the training plan themselves, or granted access to the coach to upload the training plan to their athlete profile. To complete the process of associating the training plan with the athlete profile, data from the training plan is preferably tagged for inclusion in fields reserved for training plan data. Thereafter, the athlete may view the uploaded training plan in their athlete profile. Processor 104 is preferably configured to send a notice to the athlete once the training plan has been uploaded and associated with the athlete profile. The notice may take many forms, for example, an e-mail, text message, or other forms of electronic messaging and/or print notification.

The training plan preferably includes at least one workout. More preferably, the training plan includes a plurality of workouts configured to be completed over a predetermined interval of time. For example, a coach may have a training plan that includes one to three workouts over a predetermined number of days, months or seasons. It will be appreciated that only a single workout may be uploaded at a time if desired. For example, a coach may wish to upload a single workout per a day to the athlete profile.

Preferably, the athlete receives notification that a new training plan or workout has been associated with their athlete profile. The athlete logs onto the platform, views their athlete profile, and takes note of the training plan or workout uploaded to the athlete profile by their coach. The athlete may then perform a scheduled workout, and after the workout, enter aspects of the completed workout into training log 124 to update the training record.

Examples of fields used in the training record are illustrated in FIG. 4 and may include a field corresponding to a distance aspect and/or a time aspect of the workout. The distance aspect may include the distance covered by the athlete during a training run or ride, or swum by an athlete in a body of water. The time aspect may include the interval of time to cover the distance trained. It will be appreciated that the distance and/or time may be sub-divided without departing from the scope of the present invention. For example, during a track workout, an athlete may record a plurality of timed distances. It will be appreciated that the training record may be configured with many fields including, but not limited to activity type (e.g., running, swimming, cycling, weight training), route, venue (e.g., city, park or pool), heart rate, and/or weather conditions.

After the athlete updates the training record via training log 124, processor 104 preferably notifies the coach that the athlete has completed a workout. The notification may take any of the forms described above in relation to the notification provided to the athlete of the presence of the training plan or workout.

The coach, after viewing the training record of the athlete, may alter an existing training plan on the athlete profile, or replace the existing training plan with a new training plan. It will be appreciated that if only a single workout is associated with the athlete profile, processor 104 may be configured to automatically delete the planned workout from the athlete profile once the athlete enters data indicating that the planned workout was completed. Likewise, at the end of a planned training cycle, the training plan may be automatically deleted from the athlete profile once all workouts have been completed.

Figure 8:
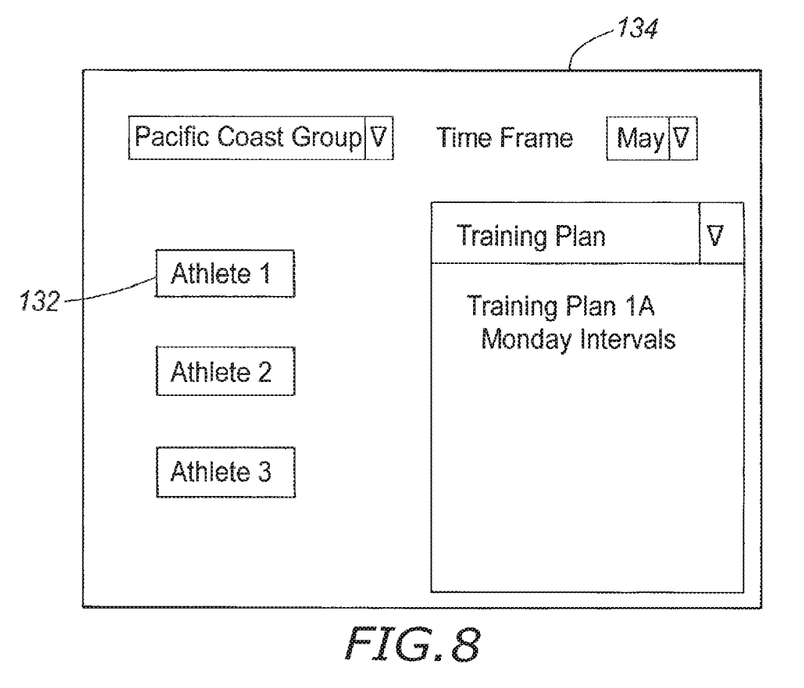
FIG. 8 is a preferred embodiment of a graphical user interface for use in generating a coaching dashboard in accordance with another preferred embodiment of the present invention.
Figure 9:
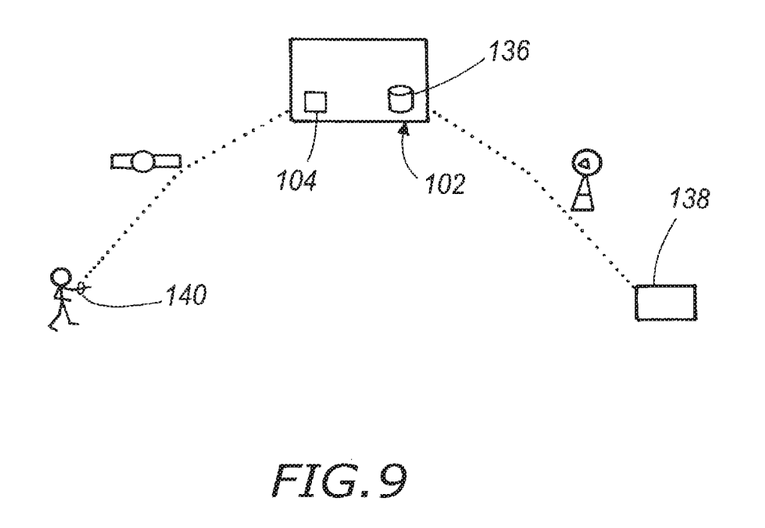
FIG. 9 is system pictoral diagram showing the interaction between a user, the platform of FIG. 1, and a local workstation of a coach.

Referring to FIGS. 8 and 9, on the provider side of the training gateway, a provider such as a coach preferably accesses one or more athlete profiles 132 through a user interface generated by processor 104 as a coaching dashboard 134. The coaching dashboard preferably includes a link to each athlete profile which the coach is authorized to access. Coaching dashboard 134 preferably includes a link to a training plan database 136, which is preferably maintained by platform 102 as shown in FIG. 9. Training plan database 136 preferably is configured to store one or more training plans or workouts. It will be appreciated that the training plan database may be locally maintained at a workstation 138 of the coach.

Referring to FIG. 8, the coach, preferably taking into account the demographics and goals of the athlete, preferably designs or selects a training plan or workout for the athlete, and through the dashboard, uploads the training plan or workout to the selected athlete profile. After being notified that the athlete has completed the training cycle associated with the training plan, or one or more workouts, the coach may modify an existing plan on the athlete profile, or completely replace an existing training plan or workout in the athlete profile with a new training plan or workout. The coach may associate a training plan or workout for a single athlete, a plurality of individual athletes, and/or a group of athletes simultaneously. For example, in FIG. 8, the training group Pacific Coast Group is selected via a pull down menu, and a time frame for the month of May is selected with a training plan (training plan 1A) for athletes 1, 2 and 3, who are members of the Pacific Coast Group. Athletes 1, 2 and 3 may be co-located in the same geographic vicinity, or widely dispersed around the country.

As shown in FIG. 1, platform 102 preferably includes a rankings generator 120. Details of a preferred rankings generator are found in U.S. application Ser. No. 13/484,213, filed May 30, 2012, entitled "System and Method for Providing an Athlete with a Performance Profile," the entire disclosure of which is incorporated by reference herein.

Referring to FIG. 1, platform 102 may be configured to permit media content providers to upload to media database 114 media specific to a registered user, which the registered user may access once logged-in. Details of a preferred medial portal are found in U.S. application Ser. No. 13/484, 213.

Platform 102 is preferably programmed to automatically notify a registered user, more preferably, a subscriber, upon the uploading of results into results database 110. Platform 102 is further preferably configured to automatically notify a registered user upon the availability of media specific to the registered user. The media may become available upon uploading the media to the media database, or by a media content provider leaving an indication in the registered user's account that the media is available for access through a link to the media provider's website.

The foregoing description is by way of example only, and may be varied considerably without departing from the scope of the present invention. For example only, the platform may be optimized for use with hand-held mobile devices. For example, a registered user may access their own training log while at the gym or immediately after a workout and update their training log remotely. Additionally, the training log may be updated automatically with a GPS device in sync with training log feature 124. For example, a cyclist or runner may wear a GPS-enabled device which is Internet ready so that as the user is training, training data is being communicated "live" to the user's personal training log on the platform. Upon finishing the training activity, the user may access a summary of the training activity. It will be appreciated that the device may communicate with the platform only after the training activity is complete to do a data dump in order to reduce Internet usage.

The training gateway may be varied without departing from the scope of the present invention. For example only, referring to FIG. 9, an athlete may wear a tracking device 140, such as a GPS enabled tracking device, that provides live updates to platform 102. Coaching dashboard 134 may be configured to provide the coach with live training information as the athlete is performing the workout. It will be appreciated that the live data feed provided by the tracking device may be used to monitor an athlete's performance during a competition and provide the coach with live data on the progress of the athlete during the competition. An example of a system for providing a live feed to a training log is described in U.S. Provisional Application No. 61/705, 232, filed Sep. 25, 2012, entitled "Interface and Method for Updating an Athlete Training Log," the entire disclosure of which is incorporated by reference herein.

In another preferred aspect, a system and method for transferring an athlete's training data from a bike computer to an online training log associated with the athlete is set forth. The system includes a mobile training computer, a mobile communications device, and a computer web-based platform. The preferred components of the system and their interaction with each other are described further below.

The mobile training computer preferably includes a processor, a memory and a transceiver. Structurally, the mobile training computer is preferably sized and configured to be mounted on a user's bike. More preferably, the mobile training computer is adapted to be worn on the wrist of the user, and configured to be detached from the user and attached to the bike. The mobile training computer preferably includes Global Positioning System (GPS) hardware configured to permit the processor to track the position of the user throughout the duration of a training session, whether in the water or on land.

The transceiver is preferably a peer-to-peer wireless communications radio. Preferably, the transceiver is configured to utilize Wi-Fi Direct to establish a peer-to-peer communications link with the mobile communications device. It will be appreciated that the transceiver may be configured to utilize other peer-to-peer communications protocols without departing from the scope of the present invention. For example only, the transceiver may be configured to utilize Bluetooth and/or near field communications. The specific details of the Wi-Fi Direct, Bluetooth and near field communications protocols would be appreciated by those of ordinary skill in the art and therefore are not repeated here.

The mobile communications device is preferably a personal device such as a smart phone or tablet. Preferably, the mobile communications device is capable of establishing a wireless communications link using a communications network such as a satellite or cellular network. It will be appreciated that the mobile communications device may be configured to transfer data without utilizing a cellular network, for example only, by utilizing a local Wi-Fi network.

The platform is preferably a computer web-based system accessible by the user through the Internet. The platform includes a processor and a training log server configured to store a plurality of user profiles. It will be appreciated that although data is shown stored at a remote location on the platform, data may also be stored in a cloud, or at one or more locations physically remote from the processor.

In another preferred aspect, an exemplary method for transferring data from the mobile training computer and updating the user's online training log stored at training the log server is set forth. A peer-to-peer communications link is established between the mobile training computer and the mobile communications device. Preferably, the communications link is established utilizing a peer-to-peer transceiver located in the mobile training computer. More preferably, the communications link is established using Wi-Fi Direct, Bluetooth or near field communications. Next, the training data stored on the mobile training computer is transferred to the mobile communications device using the peer-to-peer communications link. The training data is then formatted for transfer from the mobile communications device to the web-based platform. Thereafter, the formatted training data is uploaded to the web-based platform to update the online training log of the user.

It will be appreciated that the steps described above may be performed in a different order, varied, or certain steps omitted entirely without departing from the scope of the present invention. For example only, the data transferred from the mobile training computer may be transferred onto the online training log without any special formatting. If desired, training data may be transferred using an ordinary Wi-Fi connection between the mobile training computer and the platform. For example, the mobile training computer may be detached from the wrist of the user or the mount on the bike, and brought within a Wi-Fi hotspot. Thereafter, the training information may be uploaded into the user's online training log.

The mobile training computer may be fitted with a non-peer-to-peer wireless communications link capable of accessing the Internet. For example, the mobile training computer may be fitted with a conventional Wi-Fi radio instead of, or in addition to a peer-to-peer configured radio transceiver. The mobile communications device may be fitted with a peer-to-peer configured radio transceiver. A peer-to-peer link may be established using either the mobile communications device or the mobile training computer.

The mobile training computer may be worn on the user, for example, with a body strap at the wrist or about the user's chest. In the latter example, the mobile training computer may be configured to transmit information for display on a bike computer on the user's bike. As most of the circuitry is being worn by the user, the size of the bike computer may be greatly reduced, essentially to a display with a minimum of circuitry necessary to receive a data stream from the wearable mobile training computer. The mobile training computer may be configured to be worn on other areas of the body, such as the ankle or around the head.

The "Summary" function may be modified to provide visual representations of training history in terms of pie charts and other visual aids. Additional fields may be added for weight, heart rate, difficulty rating and weather if desired. Annual reports may be generated and printed for each registered user as desired.

The "Equipment Tracker" function may be modified to allow a user to enter their own equipment for tracking. Additionally, a "notes" field may be provided to permit the user to describe the brand of equipment, or other information as desired by the user. The warning distance feature may be configured to send a notification to the user via an electronic communication such as e-mail or texting.

If desired, the warning described above may appear on the display of the mobile training computer. The warning may be transferred to the mobile training computer through the communications link established between the mobile communications device and the platform and/or between the communications device and the mobile training computer. Various parameters may be tracked by the mobile training computer and the warning distance stored locally by the mobile training computer and displayed on its display.

The personalized calendar feature may be configured to determine if a registered user is within a predetermined distance from a competition, and provide the user with information regarding hotels and restaurants within a predetermined radius of the site of the competition. For example, if a registered user lives 75 miles away from a competition for which the user entered, the platform may send or e-mail the user information on all hotels within a 5 mile radius of the site of the competition. Moreover, the platform may be configured to determine vacancy information for the hotels and provide the user with hotel information for hotels still having vacancy. The platform may be configured to notify a registered user of the forecasted weather at the site of the competition a set number of days before the competition, for example, one, two and/or three days before the competition date. The weather forecast may include hourly forecasts if desired.

The platform may be configured for use with activities other than running, cycling, swimming or multisport. For example only, the platform may be configured for use with weight training, kayaking, crew, hiking, mountain climbing, golf, tennis, martial arts, and other sports.

Information normally stored at a physical location may be stored in a cloud, considerably reducing the hardware needed for memory requirements often associated with large volumes of data.

The features described with respect to one embodiment may be applied to other embodiments, or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for providing a coach with live training data of an athlete as the athlete is performing a cycling workout, the method comprising:
   creating an athlete profile on a training log server of a computer web-based platform, the training log server being configured to maintain a plurality of athlete profiles, the athlete profile including a training record having a plurality predefined fields, at least one of the fields corresponding to a distance aspect of an athlete's workout, at least another of the fields corresponding to a time aspect of the athlete's workout;
   updating, at the platform, a training record in the athlete profile with workout data from a mobile tracking device worn by the athlete around a portion of a head of an athlete as the athlete is performing the cycling workout, the workout data including a distance aspect and a time aspect; and
   permitting the coach to log onto the platform and view the training record of the athlete profile as the athlete is performing the cycling workout.

2. The method of claim 1, further comprising receiving, at the platform, at least one workout created by the selected coach and associating the workout with the athlete profile.

3. The method of claim 2, further comprising comparing the workout data for a given day with a planned workout forming part of a training plan and determining whether the athlete completed the workout as planned.

4. The method of claim 3, further comprising generating a graphical representation comparing the athlete's actual workout to the planned workout.

5. The method of claim 3, further comprising automatically deleting the workout after receiving an indication that the workout was completed by the athlete.

6. The method of claim 1, wherein the updating of the training record includes calculating a cumulative training distance for a selected interval of time using the distance aspect of the workout data from the athlete.

7. The method of claim 1, further comprising generating a calendar and populating the calendar with portions of a training plan.

8. The method of claim 1, where the tracking device is a GPS-enabled tracking device.

9. The method of claim 1, further comprising monitoring the athlete's performance during a competition and providing the coach with live data on the progress of the athlete during the competition.

10. The method of claim 1, further comprising receiving from the athlete a selection of a coach who is to be granted access to the athlete's profile.

11. The method of claim 10, further comprising presenting the athlete an option to grant access to the athlete profile to the coach selected by the athlete; and receiving, at the platform, the grant of access by the athlete for the selected coach to the athlete profile.

12. The method of claim 1, wherein the mobile tracking device includes a first wireless communications radio configured for peer-to-peer communications, and a second wireless communications radio configured for non-peer-to-peer communications.

13. The method of claim 12, wherein the first wireless communications radio is configured for peer-to-peer communications with a smart phone.

14. The method of claim 12, wherein the second wireless communications radio is configured to access the internet through a Wi-Fi connection to facilitate syncing of the mobile tracking device with an online training log.

15. The method of claim 1, wherein the mobile tracking device includes GPS circuitry configured to enable live updating of an online training log as the athlete is training.

16. The method of claim 1, further comprising permitting the athlete to selectively restrict access by the coach to portions of the training record.

17. The method of claim 1, further comprising tracking usage of a pair of bicycle tires.

18. The method of claim 1, wherein the coach is a person.

19. A wearable mobile training computer configured to sync with an online training log of an athlete as the athlete is cycling, comprising:
a processor, GPS circuitry configured to permit said processor to track the athlete throughout a duration of a cycling session, a memory, and a wireless communications radio configured to communicate with a mobile communications device, said wearable mobile training computer being configured to be worn around a portion of a head of the athlete, the GPS circuitry being configured to enable live updating of the online training log as the athlete is cycling.

20. The wearable mobile training computer of claim 19, wherein said wireless communications radio is configured for peer-to-peer communications with the mobile communications device.

* * * * *